United States Patent
Nozaki

(10) Patent No.: US 7,897,321 B2
(45) Date of Patent: Mar. 1, 2011

(54) MONOMER, RESIN, RESIST COMPOSITION USING THE RESIN, AND METHOD PRODUCING SEMICONDUCTOR DEVICE USING THE RESIST COMPOSITION

(75) Inventor: Koji Nozaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 235 days.

(21) Appl. No.: 12/360,292

(22) Filed: Jan. 27, 2009

(65) Prior Publication Data
US 2009/0191485 A1    Jul. 30, 2009

(30) Foreign Application Priority Data
Jan. 28, 2008   (JP) .................. 2008-016296

(51) Int. Cl.
| G03F 7/039 | (2006.01) |
| G03F 7/20 | (2006.01) |
| G03F 7/30 | (2006.01) |
| C08F 28/06 | (2006.01) |
| C07D 335/02 | (2006.01) |

(52) U.S. Cl. ................ 430/270.1; 430/325; 430/326; 430/910; 526/256; 549/13; 549/28

(58) Field of Classification Search .............. None
See application file for complete search history.

(56) References Cited

U.S. PATENT DOCUMENTS
| 7,049,044 B2 | 5/2006 | Gonsalves et al. |
| 2007/0111140 A1 | 5/2007 | Hatakeyama et al. |
| 2007/0123674 A1 | 5/2007 | Yamada et al. |
| 2007/0149702 A1 | 6/2007 | Ando et al. |

FOREIGN PATENT DOCUMENTS
| JP | 2004-162040 A | 6/2004 |
| JP | 2007-161987 A | 6/2007 |
| JP | 2007-197718 A | 8/2007 |

*Primary Examiner* — Sin J. Lee
(74) *Attorney, Agent, or Firm* — Westerman, Hattori, Daniels & Adrian, LLP

(57) ABSTRACT

A monomer, which is represented by General Formula I:

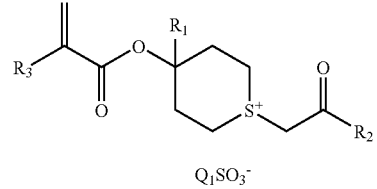

General Formula I wherein, each of $R_1$ and $R_3$ is either —H group or —CH$_3$ group, and $R_1$ and $R_3$ are identical or different to each other; $R_2$ is either a phenyl group or an adamanthyl group; and Q1 is a C1-4 perfluoroalkyl group.

7 Claims, 5 Drawing Sheets

MONOMER, RESIN, RESIST COMPOSITION USING THE RESIN, AND METHOD PRODUCING SEMICONDUCTOR DEVICE USING THE RESIST COMPOSITION

CROSS-REFERENCE TO RELATED APPLICATIONS

This application is based upon and claims the benefits of the priority from the prior Japanese Patent Application No. 2008-16296 filed on Jan. 28, 2008, the entire contents of which are incorporated herein by reference.

FIELD

The embodiments discussed herein are related to a novel monomer, a resin which contains the monomer as a constitutional unit and includes a sulfonium salt-containing side chain, a resist composition using the resin, and a method for manufacturing a semiconductor device using the resist composition. The embodiments describe the monomer, resin, resist composition and method for manufacturing a semiconductor device, wherein the resin itself has a site that produces acid as a result of decomposition due to light exposure, an acid generating agent is evenly distributed in a formed film, and thus a fine pattern can be formed at high sensitivity while preventing elution or out gassing.

BACKGROUND

In the current technology of the semiconductor integrated circuit, higher integration has been achieved and as a result, the minimum pattern size reaches the region of 100 nm or less. For the formation of fine patterns, exposure technique is regarded as very important, and the exposure technique enables to attain a desired pattern in the following manner. At first, a resist film is applied onto a substrate to be processed (surface to be processed) to which a thin film has been formed, the resist film is selectively exposed with light and then developed so as to form a pattern, a dry etching is performed using the thus obtained pattern as a mask, and finally the resist pattern is removed to thereby obtain the desired pattern.

In order to realize downsizing of the pattern, it is effective to improve and develop both an exposure light source using the shorten wavelength and a resist material of high resolution corresponding to the characteristics of the exposure light source. Currently, ArF excimer laser exposure tools have been on the market. However, these exposure tools themselves are quite expensive and a large scale of cost is expected at the time the exposure tool is updated for the purpose of shortening the wavelength of the exposure tool. Moreover, it is not easy to develop a resist material which corresponds to the shorten wavelength of exposure light, and it is extremely difficult to realize the downsizing of the pattern by only shortening the wavelength of the exposure device.

For these reasons, attentions have been attracted to a new exposure technique, a liquid immersion exposure method, in the art. In this method, the space between the projection lens and wafer in the exposure device is filled with a liquid having a lager refractive index n than that of air so as to improve and obtain higher resolution than that of the related art.

The resolution of the exposure device is determined by using the following Calculation Formula 1:

Resolution $R$=Coefficient $k$×Wavelength $\lambda$ of light source/Numerical aperture NA     Calculation Formula 1

As represented with Calculation Formula 1, the resolution R improves (be smaller), as the wavelength $\lambda$ of an exposure light source is shorter and the numerical aperture NA is larger. Note that, the numerical aperture of the projection lens is represented as: NA=n×sin $\alpha$, where n is refractive index of a medium through which the exposure light is transmitted, and $\alpha$ is an angle formed between the exposure light and a light axis of the projection lens. Since the exposure of light is generally performed in atmospheric air, the refractive index n is 1 (i.e., n=1). The liquid immersion exposure method applies the exposure system in which the space between the projection lens and the wafer is filled with a liquid having the refractive index n larger than 1 (i.e., n>1). Accordingly, the refractive index is enlarged from 1 to n (a number larger than 1) in the relative formula of the numerical aperture NA: NA=n×sin $\alpha$. At the incident angle $\alpha$ of the same exposure light, the resolution R (minimum resolution size) will be reduced in 1/n as NA is enlarged n time(s). In addition, there is also the advantage such that, in the case where the value of NA is set the same, the focal depth is deepened n times as a can be reduced by enlarging n.

The liquid immersion exposure method, which uses the liquid having larger refractive index than that of air, is a known technique in the field of microscopy. However, the development of this method for the application of the fine processing technology has just begun, and the problems have gradually been clear in the course of the development. One of the sever problems is such that the sensitivity of the resist material is lowered as the acid generated within the resist film at the time of the exposure is released (eluted) in liquid, e.g. water, as the resist film is exposed with the water present between the projection lens and the wafer. Moreover, in the case where the excimer laser is transmitted to the resist film in the state where the water is penetrated in the resist film, the inherent characteristics of the resist material is ruined due to the chemical reaction, which would not be caused in the conventional dry atmosphere, or the eluted substance will be a factor to cause the contamination of the lens or the like of the exposure device.

Other than the technique mentioned above, the fine processing technique using a EUV (i.e., extreme ultraviolet ray, wavelength: 13.5 nm) light source has been vigorously developed as the exposure technique for the next generation. Recently, the exposure device called $\alpha$-demonstration tool has begun to run experimentally. The environment for the development of the resist material for this technique has also been gradually prepared. Accordingly, there is also a demand for a development of a resist material corresponding to the EUV exposure technology which is performed in a highly vacuumed atmosphere. One of the biggest challenges for carrying out the exposure in highly vacuumed atmosphere is to maintain the characteristics, e.g. sensitivity, resolution, less roughness etc., of the resist material, at the same time as reducing the degassing (out gassing) from the resist film. If the amount of the out gassing is large, the contamination is accumulated on the reflective projection optical system, and thus reflectivity of the optical mirror is reduced. In this regard, the development of the resist material which reduces out gassing as much as possible is the urgent need. As a result of recent researches, it has been found and noted that the acid generating agent contained in the chemical amplified resist material is decomposed by the exposure light, and this decomposed product is a source for out gassing which significantly contaminates the mirror.

It has been pointed out the possibility that the source of the contamination for the lens or the like in the process of the liquid immersion exposure is a decomposed product of a cation site, which is produced by the exposures, not the anion site of the acid generating agent which is conventionally determined by LC-MS. Therefore, there has been a demand for the acid generating agent having such structure that the cation site is not easily eluted. Moreover, in the process of the EUV exposure, there is a report which informs that the main factor for contaminating the mirror is considered to be a hydrocarbon substance. Therefore, the structure of the cation site of the acid generating agent is preferably modified in either of the exposure methods.

As mentioned above, the consideration is given to the prevention of contaminating the exposure device or the like due to the main factor of the acid generating agent contained in the resist material itself in both liquid immersion exposure method and EUV exposure method. However, if the content of the acid generating agent is merely reduced, the sensitivity or resolution may be lowered. Therefore, such method may not be acceptable as a solution. There is also an attempt for reducing the aforementioned elution or out gassing by optimizing the structure of the acid generating agent. However, the optimization of the structure and the lithographic performance are difficult to attain at the same time, and thus it may take a long period of time to develop such the acid generating agent.

In order to solve these problems, there has been proposed a method for reducing elution or out gassing, in which an acid generating side chain is introduced into a base resin itself, not adding the acid generating agent as in the conventional manner, and this method has been remarked as a one of the effective solutions (see, for example, Japanese Patent Application Laid-Open (JP-A) Nos. 2004-162040, 2007-161987, and 2007-197718, and U.S. Pat. No. 7,049,044). It has been known that the acid generating side chain is capable of functioning in a small amount thereof compared to the addition of the conventional acid generating agent since the acid generating side chain is closely present to an acid liable group in the polymer side chain, as well as that the acid generating side chains are uniformly present in the resist film. Therefore, such acid generating side chain effectively works for reducing out gassing or elution. However, not so many variations of monomer having such acid generating side chain or resin using the same are known. In addition, most of them contain aromatic rings, and thus there is a problem such that the transparency can be lowered at ArF wavelength. Therefore, there has been a demand for a widened selection of materials, and a development of the material which is easily produced. Furthermore, as mentioned above, it has not been yet known any material having a structure in which a cation site is not easily eluted or out-gassed, together with the structure mentioned above.

SUMMARY

The present invention aims at solving the problems present in the art, and achieving the following objects.

Accordingly, it is an object in one aspect of the invention to provide a resin including a sulfonium salt-containing side chain as an acid generating side chain which does not impair transparency or sensitivity of a resist composition and has less possibility to cause elution or out gassing that is a factor of contamination of an exposure device, as well as providing a monomer compound.

It is another object in another aspect of the invention to provide a resist composition using the resin, and a method for producing a semiconductor device wherein a fine resist pattern is formed using the resist composition.

According to an aspect of the invention, a monomer is represented by General Formula 1:

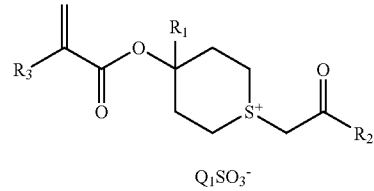

General Formula I wherein, each of $R_1$ and $R_3$ is either —H group or —$CH_3$ group, and $R_1$ and $R_3$ are identical or different to each other; $R_2$ is either a phenyl group or an adamanthyl group; and Q1 is a C1-4 perfluoroalkyl group.

The monomer contains a sulfonium salt therein, and a resin formed by using the monomer as a constitutional unit is preferably introduced in a resist base resin at least a part thereof. In such resist base resin, the acid generating side chain is capable of functioning in a small amount thereof since the acid generating side chain is closely present to an acid labile group of the polymer side chain, as well as that the acid generating side chains are uniformly present in the resist film. Therefore, the risks of elution or out gassing which will contaminate an exposure device can be reduced, without impairing transparency or sensitivity.

According to another aspect of the invention, a resin contains the monomer unit (as a constitutional unit), and includes a sulfonium salt-containing side chain therein.

The resin includes the sulfonium salt-containing side chain, and is preferably introduced in a resist base resin at least a part thereof. In such resist base resin, the acid generating side chain is capable of functioning in a small amount thereof since the acid generating side chain is closely present to an acid labile group of the polymer side chain, as well as that the acid generating side chains are uniformly present in the resist film. Therefore, the risks of elution or out gassing which will contaminate an exposure device can be reduced, without impairing transparency or sensitivity.

According to another aspect of the invention, a resist composition contains the resin at least in the part of a resist base resin.

In the resist composition, the resist base resin contains the resin at least a part thereof. In such resist base resin, the acid generating side chain is capable of functioning in a small amount thereof since the acid generating side chain is closely present to an acid labile group of the polymer side chain, as well as that the acid generating side chains are uniformly present in the resist film. Therefore, the risks of elution or out gassing which will contaminate exposure device can be reduced, without impairing transparency or sensitivity.

According to another aspect of the invention, a method for producing a semiconductor device contains: forming a resist film which is formed from the resist composition on a surface to be processed; selectively exposing the resist film with exposure light under an atmospheric air, a vacuum condition, or liquid immersion; and developing the resist film so as to form a pattern of the resist film.

In accordance with the method for producing a semiconductor, the resist film is formed on the surface to be processed by using the resist composition, the resist film is selectively exposed with the exposure light under the atmospheric air, the vacuum condition or the liquid immersion, and the resist film is developed to thereby form the resist pattern.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS (Monomer)

Figure 1:
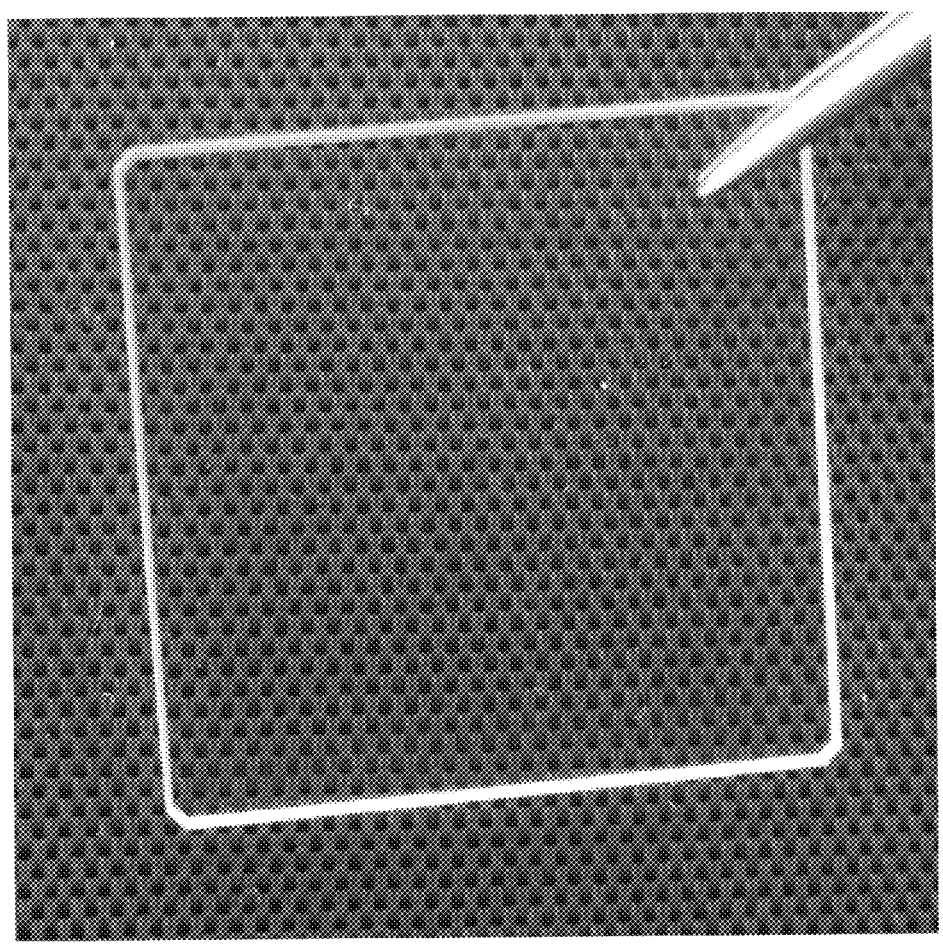
FIG. 1 is a picture showing the result of a simplified lens contaminating test using Monomer II.

The monomer of the present invention is a compound represented by General Formula 1. This monomer reduces elution or out gassing as a result of the structure such that a sulfonium cation site of the monomer will be present at a side chain of the resulted resin formed by polymerization. Hereinafter, the monomer and forming method thereof will be described.

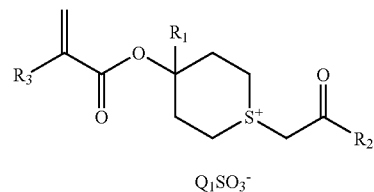

General Formula I

In General Formula 1, each of $R_1$ and $R_3$ is either —H group or —$CH_3$ group, and $R_1$ and $R_3$ are identical or different to each other. In addition, a trifluoromethyl group may also be suitably used as $R_3$. In General Formula 1, $R_2$ is preferably selected from a phenyl group, an adamanthyl group and the derivatives thereof. The thiopyran ring may contain a ketone group at $\alpha$- or $\beta$-position of sulfur atom. In General Formula 1, $Q_1$ is a C1-4 perfluoroalkyl group or the like. Moreover, $Q_1SO_3^-$ is, for example, perfluoroalkane sulfonic acid anion containing $Q_1$, anion of perfluorodisulfone imide, or anion of bistrifluoromethane sulfone imide.

Examples of such monomer include compounds represented below. In the formulae shown below, anion $Y^-$ indicates anion of perfluoroalkyl suofonic acid, disulfone imide, bisulfone imide represented as follows:

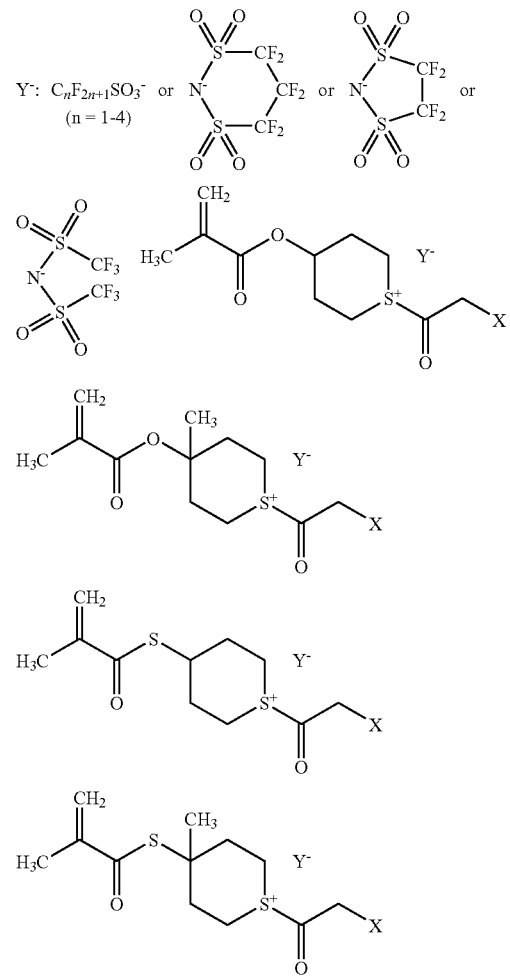

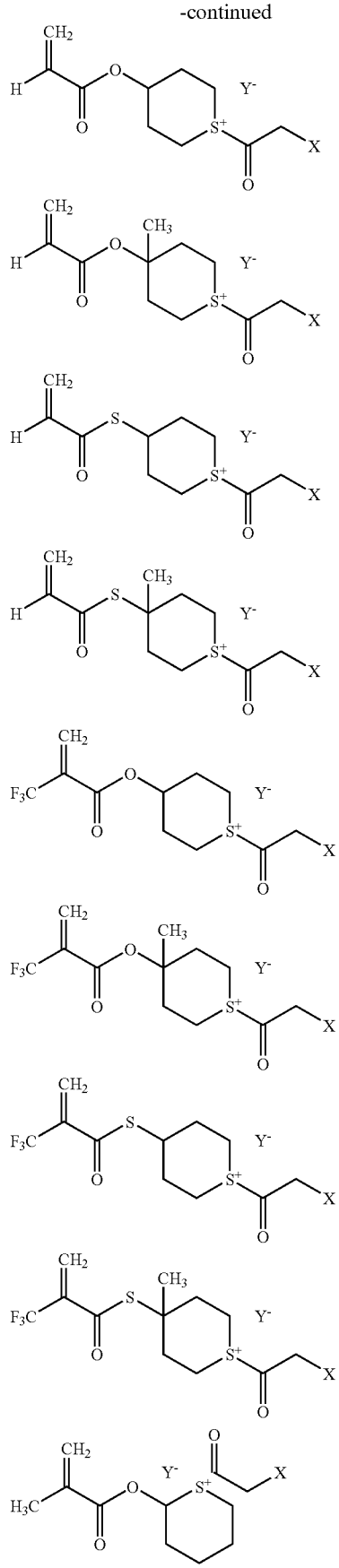
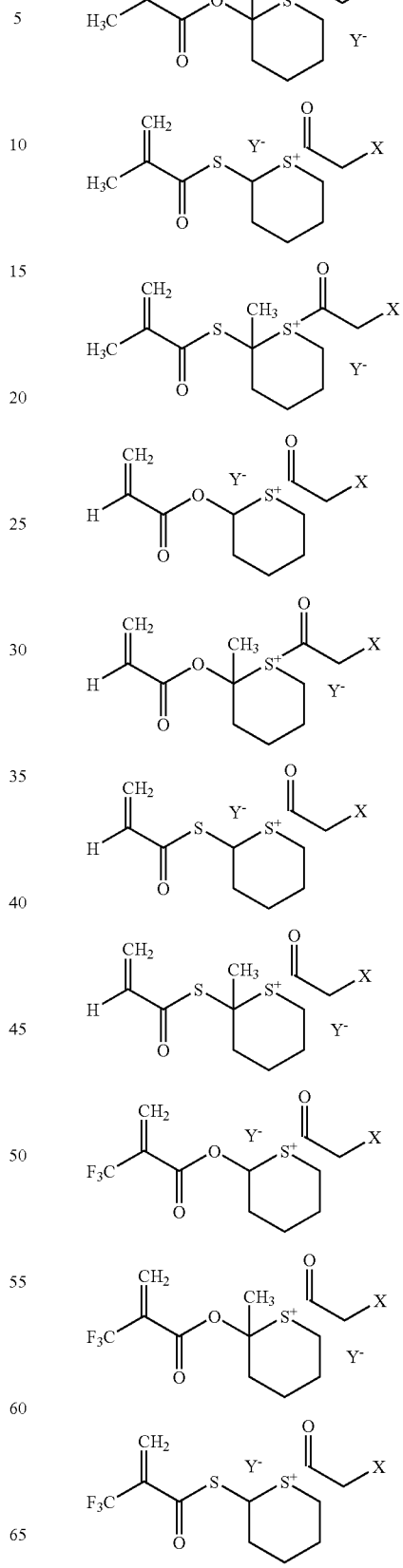

-continued

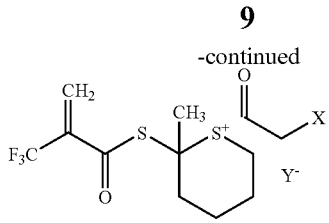

<Forming Method of Monomer>

These monomers may be synthesized in accordance with any of methods known in the art. The monomer precursor having thiopyran at a site which will be a side chain in the resulted resin is generally formed by an esterification reaction of the corresponding acid chloride and alcohol, or the corresponding acid chloride and thiol. Specifically, for example, the same molar amounts of an alcohol or a thiol and a basic catalyst such as triethylamine are added in a solvent such as a dried methylene chloride, the mixed solution is cooled to the temperature of 0° C. to −20° C., acrylchloride is added dropwise through a dropping funnel while stirring, and then disappearance of the raw materials is confirmed with a thin film chromatography or gas chromatography. Thereafter, triethyl amine salt is removed, and the reaction mixture is purified using a column chromatography to thereby easily obtain the ester.

The thus obtained monomer precursor is mixed with, for example, phenacyl bromide in acetonitrile or nitromethan at room temperature, to thereby obtain the corresponding sulfonium bromide. With the thus obtained sulfonium bromide, for example, sodium perfluorobutane sulfonate is mixed in nitromethane at room temperature to thereby obtain the targeted product of sulfonium perfluorobutane sulfonate. Moreover, the thus obtained sulfonium perfluorobutanesulfonate can be further purified by recrystallization.

(Resin)

The resin can be suitably selected depending on the intended purpose without any restriction, provided that the resin contains the aforementioned monomer unit which includes a sulfonium salt-containing side chain. For example, the resin may be a copolymer with other monomer.

<Content of the Monomer Unit in the Resin>

The content of the monomer unit of the invention in the resin (resin for a positive resist composition) can be determined in view of transparency at the wavelength of exposure light, desirable sensitivity or resolution. It is preferably in the range of 0.1 mol % to 50 mol %, and is more preferably in the range of 1 mol % to 10 mol %.

<Other Monomers>

The other monomers copolymerized with the aforementioned monomer can be suitably selected depending on the intended purpose without any restriction, but those monomers having acid labile groups are preferable. The resin for positive resist composition itself is generally alkali-insoluble, but the resin becomes alkali-soluble after the acid labile groups are reacted.

<<Acid Labile Groups>>

The acid labile group is suitably selected from various groups used in the art depending on the intended purpose without any restriction.

Specific examples thereof include tertially ester such as t-butyl group, acetal group such as ethoxyethyl, 2-oxocyclohexyl group, 2-alkyl-2-adamantyl group, 1-alkyl-1-cyclopenthyl group, 1-alkyl-1-cyclohexyl group, 2-adamanthyloxymethyl group, 1-methyladamanthyloxymethyl group, and the like. Among them, the acid labile group having an alicyclic structure such as 2-alkyl-2-adamantyl group, 2-adamanthyloxymethyl group, or 1-methyladamanthyloxymethyl group is preferable since such acid labile group provides etching resistance and transparency at the wavelength of 193 nm. When the resulted resist composition is applied for EUV exposures, the resin preferably contains an acetal functional group, tert-butoxycarbonyl (tBOC) group or the like, together with the aforementioned acid labile group.

Moreover, the resin for a positive resist composition may preferably contain a monomer unit containing the acid labile group, and a monomer unit containing a lactone derivative. As a lactone ring is highly polar, the property contributes adhesion properties of a resist pattern, and it also imparts a suitable alkali-solubility at the exposed area due to its slight alkali-solubility.

<<Lactone Derivatives>>

A lactone derivative is suitably selected depending on the intended purpose without any restriction. Preferable examples thereof include γ-butyrolactone group, δ-lactone group, alicyclic lactone combined with norbornane or cyclohexane ring. The alicyclic lactone is particularly preferable since it contributes an etching resistance of the resulted resist composition.

In the case where the resin contains the monomer unit represented by General Formula 1, the monomer unit containing the acid labile group, and the monomer unit containing a lactone derivative, the ratio of these units is arbitral, but it is desirable that the ratio is adjusted so that both resolution and etching resistance can be attained at the same time.

Moreover, the resin for positive resist, which contains the monomer unit represented by General Formula 1 which includes the sulfonium salt-containing side chain, may further contain monomer units having other functions than mentioned above. Examples of such monomer unit include a monomer containing an alkali-soluble group such as carboxyl group or hexafluorocarbinol group at a site which will be a side chain in the resulted resin, a monomer containing a hydroxyl group such as 2-hydroxyethyl group or 3-hydroxyadamanthyl group, and the like. The amount of these monomer units in the resin should be carefully determined for desired properties such as adhesion of the resist pattern, alkali-dissolution rate of the exposed area, and the like. The resin for a positive resist composition, which contains the monomer unit represented by General Formula 1 which includes the sulfonium salt-containing side chain, may arbitrarily contain the monomer units having the aforementioned characteristics. The preferable embodiments of such resin is an acrylic resin, a hybrid resin containing norbornane monomer unit, a resin containing styrene monomer, or parahydroxystyrene monomer, or an oligomer or glass molecule of relatively low molecular weight (Mw: 2,000 or less). These preferable embodiments are appropriately selected or designed based on the total consideration of the wavelength of the exposure light, the desired etching resistance and the like.

(Resist Composition)

The resist composition is suitably selected depending on the intended purpose without any restriction, provided that the resist composition contains a resist base resin containing at least at a part thereof, the resin which contains the monomer unit represented by General Formula 1 which includes the sulfonium salt-containing side chain. In the case where the resist composition is a positive resist composition, the resist composition further contains a commonly used acid generating agent, other than the resin, so as to finely control sensitivity or resolution. The resist composition may further contain a solvent, quencher and surfactant.

<Resist Base Resin>

The resist base resin is suitably selected depending on the intended purpose without any restriction, provided that it contains the resin which contains the monomer unit represented by General Formula 1 which includes the sulfonium salt-containing side chain. The resist base resin preferably contains a monomer unit containing an alicyclic group reactive to an acid in side chain(s) thereof and a monomer unit containing a lactone group in side chain(s) thereof.

The alicyclic group reactive to an acid is suitably selected depending on the intended purpose without any restriction. Preferable examples thereof include a 2-alkyl-2-adamanthyl group, and the like.

<Acid Generating Agent>

The acid generating agent is suitably selected from those known in the art without any restriction. Preferable examples thereof include commonly used trifluoromethanesulfonium salt or perfluorobutanesulfonium salt, disulfoneimidyl salt which can be configured to have a PFAS(perfluoroalkylsulfonic acid) free structure which has been a concern for the environment, and the like. The acid generating agent is added for the purpose of assisting the base resin including the sulfonium salt-containing side chain. The amount thereof is preferably 0.01 parts by mass to 10 parts by mass with respect to 100 parts by mass of the resin, though it will be adjusted depending on the balance with the sensitivity or resolution.

<Solvent>

In the case where the resist composition is a positive resist composition, the solvent for use is appropriately selected depending on the intended purpose without any restriction provided that it is selected from the solvents generally used for resist compositions. It is preferable that the solvent for use is selected in view of the total solubility of the resin, acid generating agent, other additives and the like and the coating properties. Examples of such solvent include propylene glycol monomethylether acetate, 2-heptanone, ethyl lactate, and cyclohexanone. Optionally, an auxiliary solvent may also use. As an auxiliary solvent, propylene glycol monomethyl ether or γ-butyrolactone is used preferably, and especially an organic solvent having a boiling point of 100° C. to 200° C. and excellent solubility of the resin is used preferably. Such organic solvent is suitably used for coating as the rapid drying is prevented at the coating process.

<Quencher>

The quencher is appropriately selected depending on the intended purpose without any restriction. Preferable examples thereof include nitrogen-containing compounds such as tri-n-octyl amine, 2-methylimidazole, 1,8-diazabicyclo[5.4.0]undec-7-ene (DBU), 1,5-diazabicyclo[4.3.0]non-5-ene (DBN), diphenyl amine, triethanol amine, and the like. It has been known that the addition of the quencher contributes to improve the exposure contrast of the resist.

<Surfactant>

The surfactant is appropriately selected depending on the intended purpose without any restriction. Preferable examples thereof include nonionic surfactants free from metal ion such as sodium salt or potassium salt. Particularly preferable examples include polyoxyethylene-polyoxypropylene condensed derivatives, polyoxyalkylene alkyl ether, polyoxyethylene alkyl ether, polyoxyethylene derivative, sorbitane fatty acid ester, glycerin fatty acid ester, primary alcohol ethoxylate, phenol ethoxylate, silicone surfactant, and fluorosurfactant. Moreover, the surfactant may be selected from ionic surfactants other than the ones mentioned above, provided that the ionic surfactants are of metal salt-free. It is assumed that the same effect can be attained even if the aforementioned nonionic surfactant is replaced with such the metal salt-free ionic surfactant. The surfactant may be arbitrarily added for the purpose of the improvement mainly for the coating performance.

The examples described below explain a monomer unit containing a sulfonium salt and the method of producing the resin (polymer) which contains the aforementioned monomer unit which includes a sulfonium salt-containing side chain, but such production methods are merely one example, and the monomer can be similarly obtained in accordance with any of other conventional methods. Moreover, the examples explain a method for manufacturing a semiconductor device, but the effect of the present invention can be exhibited on the followings each having a fine pattern in the same manner. As the examples, there are listed functional parts such as a mask pattern, a reticle pattern, a magnetic head, an LCD (a liquid crystal display), a PDP (a plasma display panel), an SAW (surface acoustic wave) filter and the like, optical parts utilized for the connection of optical wirings, minute parts such as a micro actuator, and the like. Moreover, the process of the production of a flash memory is specifically explained in the examples as an example of the semiconductor device, but this method can be applied, other than the production of the flash memory, to the production of a logic device, the production of DRAM or FRAM and the like, and the same effects can be attained in those productions.

EXAMPLES

Hereinafter, the examples of the present invention will be explained, but these examples shall not be construed to limit the scope of the present invention.

The determination and evaluation of compounds were carried out by means of NMR (JNM-GX500, manufactured by JEOL Ltd.), IR (IR Prestige-21, manufactured by Shimadzu Corporation), a liquid chromatograph mass spectrometer (MS measurement) (LC-MS1100 series, manufactured by Agilent Technologies, Inc.), an ultraviolet/visible ray spectrophotometer (UV measurement) (U-3200, manufactured by Hitachi High-Technologies Corporation), and GPC (molecular weight measurement) (HLC-8200, manufactured by Tosoh Corporation).

Example 1

(Synthesis of Monomer Containing a Sulfonium Salt II)

To a 50-mL, three-necked flask fitted with a stirrer bar coated with Teflon™, was added 1.0 g of 4-methyl-tetrahydro-2H-thiopyran-4-yl methacrylate, 1.19 g of phenacylbromide, and 10 ml of acetonitrile, and the mixture was stirred at room temperature for 20 hours. The solution was gradually clouded. Thereafter, the resultant mixture was filtered through a Kiriyama funnel fitted with a filter paper under reduced pressure so as to separate a precipitate, and thus obtained precipitate was sufficiently washed with diethylether to obtain white crystals. The filtrate was concentrated in vacuo to obtain crystals, and they were dissolved in a small amount of nitromethane. To this solution, a large amount of diethylether was added, and the solution was filtered through a Kiriyama funnel fitted with a filter paper under reduced pressure so as to separate the crystals. Addition to the crystals previously obtained to give 1.47 g of Sulfonium Bromide I (yield: 73.8%).

<Result of NMR Measurement>

$^1$H-NMR (500 MHz, DMSO-$d_6$, internal standard TMS, δ in ppm): 1.55 (d, 3H), 1.92 (d, 3H), 2.19-2.7 (m, 4H), 3.49 (m, 4H), 5.55 (dd, 2H), 5.71 (m, 1H), 6.10 (d, 1H), 7.64-8.11 (m, 5H)

<Result of IR Measurement>
IR (KBr, cm$^{-1}$): 2,857, 1,715, 1,674, 1,301, 1,215, 1,169, 758

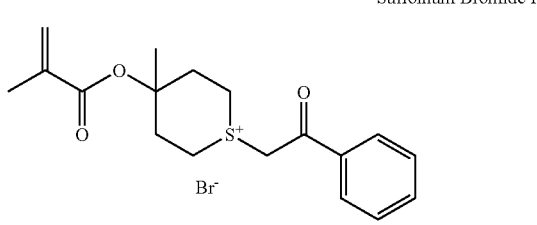

Sulfonium Bromide I

To a 200-mL, three-necked flask fitted with a stirrer bar coated with Teflon™, was added 1.47 g of Sulfonium Bromide I and 1.37 g of potassium perfluorobutane sulfonate. To this mixture, 100 mL of nitromethane was added was stirred at room temperature for 24 hours. The reaction mixture was then concentrated to approximately 50 mL in vacuo, and resultant insoluble substances were separated by filtration, and the filtrate was further concentrated. To the resultant oily residue, a small amount of MIBK was added, insoluble substances were separated therefrom by filtration, and thus obtained organic solution was then concentrated to give crystalline precipitate. After recrystallization from approximately 2 mL of butyl acetate, and the precipitate was filtered through a Kiriyama funnel fitted with a filter paper under reduced pressure to provide 0.87 g of Monomer II as white crystals (yield: 38.2%).

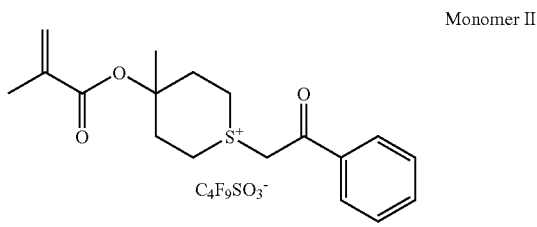

Monomer II

<Result of NMR Measurement>
$^1$H-NMR (500 MHz, DMSO-d$_6$, internal standard TMS, δ in ppm): 1.54 (s, 3H), 1.92 (s, 3H), 2.21-2.57 (m, 4H), 3.2-3.59 (m, 4H), 5.45 (s, 2H), 5.70 (s, 1H), 6.10 (s, 1H), 7.64-8.10 (m, 5H)
<Result of IR Measurement>
IR (KBr, cm$^{-1}$): 2,920, 1,713, 1,676, 1,277, 1,256, 1,132, 658
<Result of MS Measurement>
(ESI positive ion): M$^+$319 (C$_{18}$H$_{23}$O$_3$S=319.43)
(ESI negative ion): M$^-$299 (C$_4$H$_9$O$_3$S=299.09)

Example 2

(Synthesis of Monomer Containing a Sulfonium Salt IV)
To a 100-mL, three necked flask fitted with a stirrer bar coated with Teflon™, was added 1.45 g of 4-methyl-tetrahydro-2H-thiopyran-4-yl methacrylate, 2.05 g of 1-adamanthyl bromomethyl ketone, and 15 mL of acetonitril, and the mixture was stirred by at room temperature for 20 hours. Then the flask was placed into an oil bath at 40° C., and the solution was allowed to react for 6 hours. The solvent was removed in vacuo to give crystalline solid. After the addition of 30 mL diethylether, the mixture was warmed to 30° C., the crystalline solid was broken up by a spatula, and was filtered off using a Kiriyama funnel. Thus obtained precipitate was sufficiently washed with diethyl ether to obtain white crystals. The filtrate was concentrated naturally, and the thus obtained crystals were filtered off using a Kiriyama funnel. Addition to the aforementioned crystals, 2.46 g of Sulfonium Bromide III were obtained in total (yield: 74.3%).

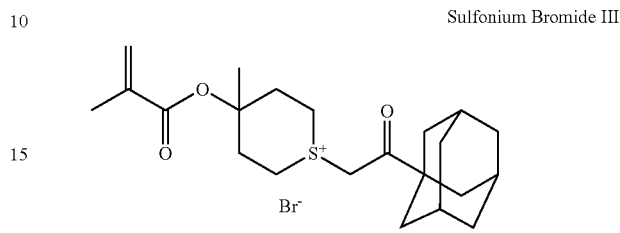

Sulfonium Bromide III

<Result of NMR Measurement>
$^1$H-NMR (500 MHz, DMSO-d$_6$, internal standard TMS, δ in ppm): 1.52 (d, 3H), 1.65 (m, 3H), 1.81 (m, 6H), 1.91 (s, 3H), 2.03 (s, 3H), 2.13-2.72 (m, 4H), 3.40 (dd, 4H), 5.01 (d, 2H), 5.70 (d, 1H), 6.09 (d, 1H)
<Result of IR Measurement>
IR (KBr, cm$^{-1}$): 2,907, 2,851, 1,718, 1,687, 1,452, 1,302, 1,165, 1,096, 1,013, 935
To a 100-mL, eggplant-shaped flask fitted with a stirrer bar coated with Teflon™, was added 2.46 g of Sulfonium Bromide III, 1.12 g of potassium trifluoromethane sulfonate, and 55 mL of nitromethane, and the mixture was stirred at room temperature for 18 hours. The solvent was removed in vacuo to obtain crystalline precipitate. Thus obtained precipitate were subjected to recrystallization using approximately 5 mL of ethyl acetate, and this solution was filtered through a Kiriyama funnel under reduced pressure to give 2.70 g of Monomer IV as white crystals (yield: 95.4%).

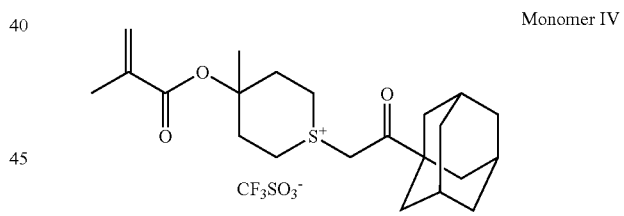

Monomer IV

<Result of NMR Measurement>
$^1$H-NMR (500 MHz, DMSO-d$_6$, internal standard TMS, δ in ppm): 1.51 (s, 3H), 1.66 (m, 6H), 1.81 (s, 6H), 1.91 (s, 3H), 2.03 (s, 3H), 2.11-2.73 (m, 4H), 3.33 (dd, 4H), 5.06 (d, 2H), 5.72 (s, 1H), 6.01 (s, 1H)
<Result of IR Measurement>
IR (KBr, cm$^{-1}$): 2,930, 1,710, 1,636, 1,250, 1,169, 1,026, 638
<Result of MS Measurement>
(ESI positive ion): M$^+$357 (C$_{22}$H$_{33}$O$_3$S=357.55)
(ESI negative ion): M$^-$149 (CF$_3$O$_3$S=149.07)

Example 3

(Synthesis of Resin Containing Monomer II Unit)
To a 100-mL, eggplant-shaped flask fitted with a dimorth condenser and a stirrer bar coated with Teflon™, was added 0.25 g of Monomer II synthesized in Example 1, 0.71 g of 2-methyl-2-adamanthyl methacrylate, 0.43 g of 3-hydroxy- 1-adamanthyl methacrylate and 0.19 g of γ-butyrolacton-3-yl methacrylate, and 4.4 mL of THF. The mixture was then stirred, and nitrogen gas was bubbled for 15 minutes to remove oxygen in the reaction atmosphere. To this was added 0.16 g of AIBN as a radical polymerization initiator, and the flask was placed in an oil bath at 60° C. for 5 hours. Thus obtained reaction mixture was cooled to room temperature and diluted with 10 mL of THF. The solution was dropped into 250 mL of hexane with stirring to give white precipitate. After filtering with a glass filter, the obtained precipitate was dried in vacuo at 50° C. for 6 hours. The resultant white powder was dissolved in approximately 10 mL of THF, was again precipitated in 250 mL of hexane, and filtered and dried using aforementioned manners to provide 1.07 g of Resin V (yield: 65.5%). The weight average molecular weight was 5,250 (linear polystyrene standard-equivalent), and the polydispersity (Mw/Mn) was 1.20.

<Result of IR Measurement>

IR (KBr disk, cm$^{-1}$): 3,443, 2,916, 2,860, 1,790, 1,721, 1,450, 1,256, 1,161, 1,101, 993

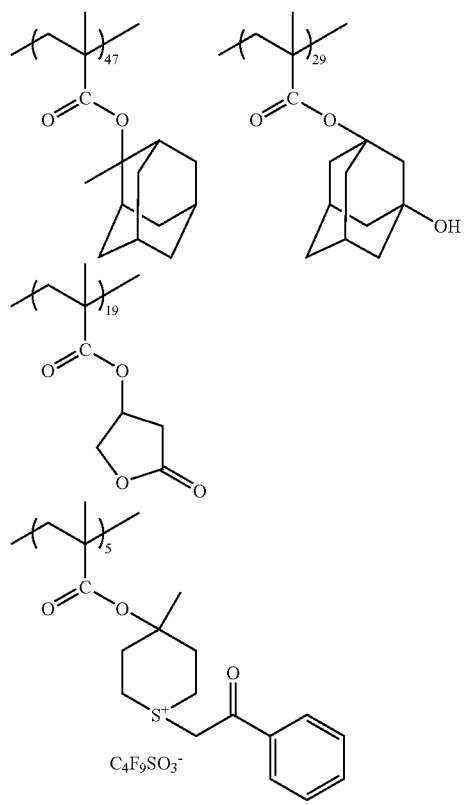

Resin V

Example 4

(Synthesis of Resin Containing Monomer IV Unit)

To a 100-mL, eggplant-shaped flask fitted with a dimorth condenser and a stirrer bar coated with Teflon™, was added 0.6 g of Monomer IV synthesized in Example 2, 1.12 g of 2-methyl-2-adamanthyl methacrylate, 0.74 g of γ-butyrolacton-3-yl methacrylate, and 7 mL of MIBK (methyl isobutyl ketone). The mixture was then stirred, and nitrogen gas was bubbled for 15 minutes to remove oxygen in the reaction atmosphere. To this was added 0.26 g of AIBN as a radical polymerization initiator, and the flask was placed in an oil bath at 60° C. for 5 hours. Thus obtained reaction mixture was cooled to room temperature, and diluted with 10 mL of THF. The solution was dropped into 300 mL of hexane with stirring to give white precipitate. After filtering with a glass filter, the obtained precipitate was dried in vacuo at 50° C. for 6 hours. The resultant white powder was dissolved in approximately 10 mL of THF, was again precipitated in 300 mL of a mixed solution of methanol and diethyl ether (5:1), and filtered and dried using aforementioned monomers to provide 0.86 g of Resin VI (yield: 36.5%). The weight average molecular weight was 3,680 (linear polystyrene standard-equivalent), and the polydispersity (Mw/Mn) was 1.14.

<Result of IR Measurement>

IR (KBr disk, cm$^{-1}$): 3,483, 2,911, 2,860, 1,789, 1,724, 1,258, 1,103, 1,030, 638

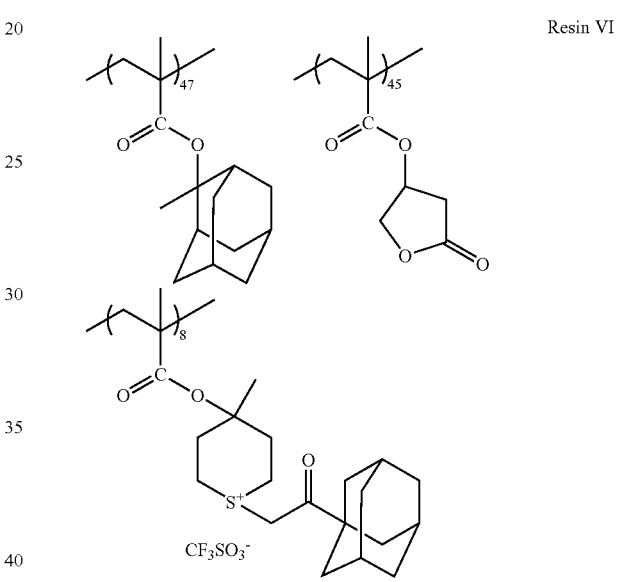

Resin VI

Example 5

(Measurement of Molar Extinction Coefficient)

Using Monomers II and IV synthesized in Examples 1 and 2, 0.1 mmol/L acetonitrile solutions were prepared respectively. Each solution was subjected to a UV measurement, and as a result, the following values were attained as presented in Table 1.

TABLE 1

| Monomer | molar extinction coefficient ε 193 nm (L/mol · cm) | molar extinction coefficient ε 248 nm (L/mol · cm) |
|---|---|---|
| II | 18,800 | 10,400 |
| IV | 11,100 | 317 |
| Com. | 60,000 | 12,600 |

For comparison the comparative monomer represented by Formula VII of the conventional acid generating agent (manufactured by Midori Kagaku Co., Ltd.) was used to prepare 0.01 mmol/L acetonitrile solution (CH$_3$CN), and the prepared solution was subjected to the measurement.

Formula VII

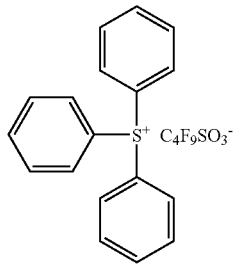

From the results represented in Table 1, it was found that the sulfonium salt containing monomers (Monomers II and IV) had smaller molar extinction coefficient which is ⅓ or less than that of the conventional acid generating agent at 193 nm, and also had smaller molar extinction coefficient than that of the conventional acid generating agent at 248 nm. Accordingly, it was found that the monomers of the invention were preferable to the conventional acid generating agent in terms of transparency.

Experimental Example 1

(Preparation of Resist Composition)

Using 3 parts by mass of each of Monomers II and IV synthesized in Examples 1 and 2 and 100 parts by mass of the resin represented by Formula VIII, resist compositions for liquid immersion exposure were prepared with the formulations represented in Table 2. As a solvent for the resist composition, PGMEA was used, and the prepared solution was filtered with a Teflon™ membrane filter having a pore size of 0.2 µm so as to prepare a coating solution for a resist film. The coating solution was spin-coated, and the coated film was baked at 110° C. for 60 seconds to thereby form a resist film. The exposure was performed by using a DUV (wavelength: 254 nm) lamp. After the exposure, PEB (post-exposure bake) was performed at the temperature indicated in Table 2 for 60 seconds. The development was performed using a 2.38% by mass TMAH developing solution.

Formula VIII

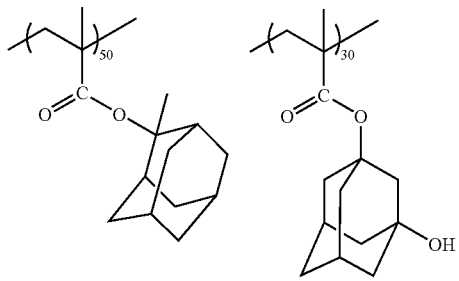

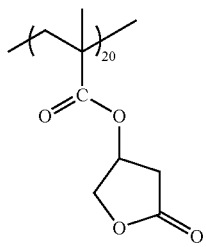

TABLE 2

| Resist Composition | Resin (parts by mass) | Monomer (parts by mass) | Solvent (parts by mass) | Sensitivity (mJ/cm2)/ PEB Tem. |
|---|---|---|---|---|
| A | VIII (100) | II (3) | PGMEA (900) | 6.6 (130° C.) |
| B | VIII (100) | IV (3) | PGMEA (900) | formation of latent image (170° C.) |

From the results of Table 2, it was understood that Monomer II functioned as an acid generating agent and Resist Composition A in which Monomer II unit was contained without adding any acid generating agent could attain sufficient sensitivity.

Although Monomer IV functioned as an acid generating agent in Resist Composition B in which Monomer IV unit was contained without adding any acid generating agent was not failed in the pattern formation, the formation of the latent image was observed. This was probably because the molar extinction coefficient of Monomer IV at 248 nm, which is the wavelength of the light used for the exposure, might have been low (transparency might have been high).

Example 6

(Preparation of Resist Composition)

Using Resins V and VI each containing the acid generating side chain synthesized in the aforementioned examples, resist compositions were prepared in the formulations indicated in Table 3, and the prepared resist composition in the form of solutions were each filtered with a Teflon™ membrane filter having a pore size of 0.2 µm. Each resist composition was spun onto a Si substrate, and then baked at 110° C. for 60 seconds to thereby form a resist film. The resist film was exposed with a DUV (wavelength: 254 nm) lamp or an ArF excimer laser exposure tool, and then subjected to PEB (post-exposure bake) at the temperature indicated in Table 3 for 60 seconds. The resist film was developed using 2.38% by mass TMAH developing solution for 60 seconds. The sensitivity $E_o$ of each resist composition was presented in Table 3.

TABLE 3

| Resist Composition | Resin (parts by mass) | Solvent (parts by mass) | SensitivityEo 254 nm (mJ/cm2)/ PEB Tem. | SensitivityEo 193 nm (mJ/cm2)/ PEB Tem. |
|---|---|---|---|---|
| D | V (100) | PGMEA(800) GBL (50) | 3.6 (130° C.) | <2 (120° C.) |
| E | VI (100) | PGMEA(800) GBL (170) | 138 (170° C.) | 45 (140° C.) |

As presented in Table 3, Resist Compositions D and E attained desirable sensitivities at 193 nm, and thus it was understood that the resin containing the acid generating side chain itself functioned as a resist composition. It was considered that Resist Composition E had a low sensitivity at 254 nm because the molar extinction coefficient of Monomer VI was low at 248 nm for use as an exposure light as described in Example 5, and accordingly the acid generating side chain contained in Resin VI had also low molar extinction coefficient.

Example 7

(Simplified Lens Contaminating Test)

Aqueous solutions (II: 10 ppm, IV: approximately 3 ppm (=saturated solution)) of the aforementioned conventional acid generating agent represented by Formula VII, Monomer II synthesized in Example 1 and Monomer IV synthesized Example 2 were respectively prepared. Each of the prepared solutions was continuously exposed with an ArF laser for one hour while being passed through a flow cell equipped with an ArF transmission glass at a flow rate of 10 mL/min. The exposure dose of the laser was 15 mW/cm$^2$ measured in a blank cell. After one hour, the flow of the solution and laser were stopped, the ArF transmission glass was removed from the flow cell, and the precipitate of the contaminant to the glass was visually determined. The results are presented in FIG. 1 (Monomer II), FIG. 2 (comparative acid generating agent VII) and Table 4.

TABLE 4

| Monomer | Condition of glass surface |
|---|---|
| II | transparent |
| IV | transparent |
| Com. | clouded |

For comparison, the comparative monomer represented by Formula VII of the conventional acid generating agent (manufactured by Midori Kagaku Co., Ltd.) was used.

Figure 2:
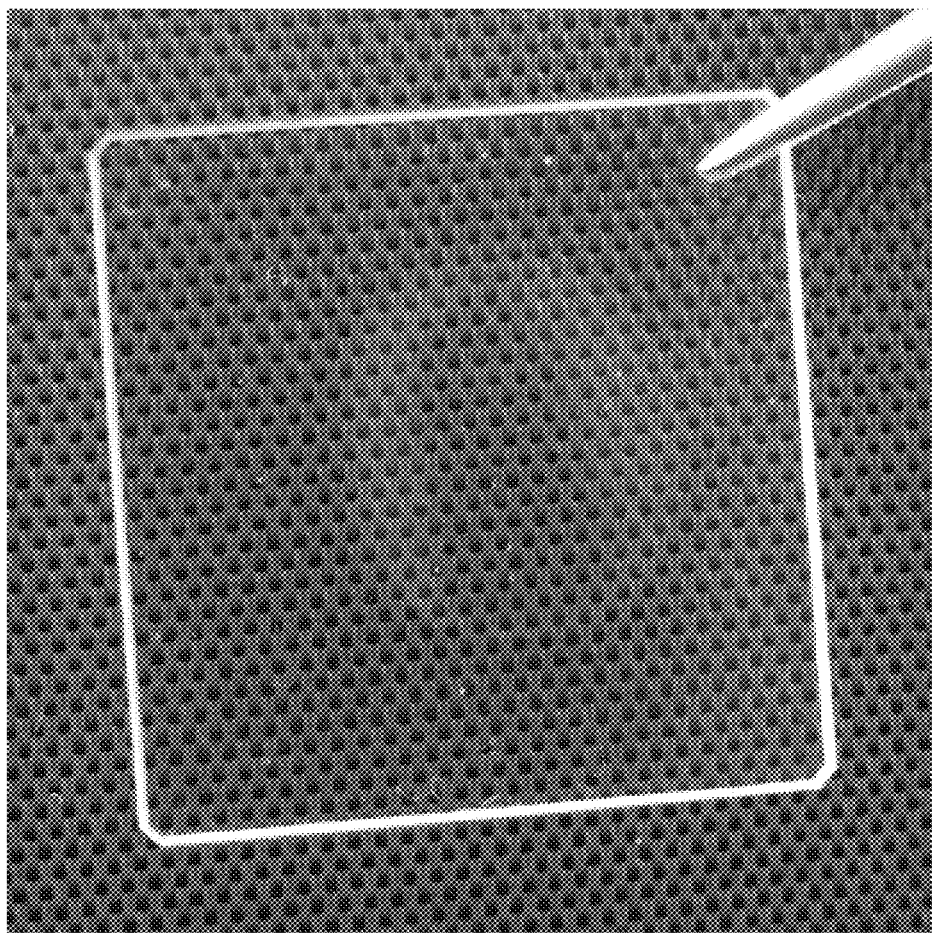
FIG. 2 is a picture showing the result of a simplified lens contaminating test using the comparative monomer.

From the results presented in FIGS. 1 and 2 and Table 4, the sulfonium salt-containing monomers did not show a clouded surface of the glass, which exemplified a lens, whereas the conventional acid generating agent showed a clouded surface of the glass. Therefore, it can be understood that the sulfonium salt-containing monomers had less contaminating properties. As a result of analyzing the cloudiness on the glass by TOF-SIMS, it was understood that the cloudiness was mainly consisted of a substance which was suspected to be a compound resulted from the photodecomposed cation portion, and such compound was insoluble or hardly soluble in water.

Example 8

(Production of Semiconductor Device)

Figure 3:
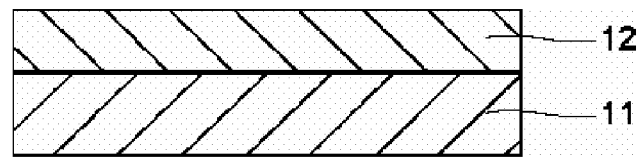
FIG. 3 is a schematic diagram explaining one example of a method for producing a semiconductor device of the invention, and illustrates a state where an interlayer insulating film is formed on a silicon substrate.
Figure 4:
FIG. 4 is a schematic diagram explaining one example of a method for producing a semiconductor device of the invention, and illustrates a state where a titanium film is formed on the interlayer insulating film of FIG. 3.
Figure 5:
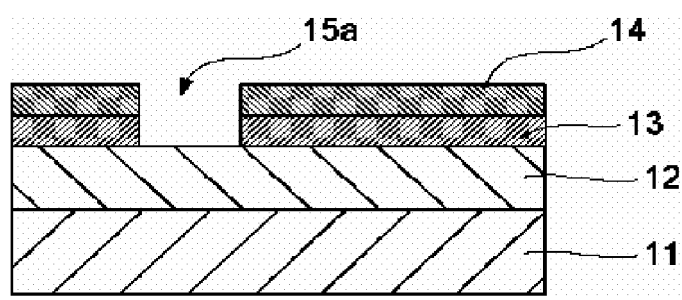
FIG. 5 is a schematic diagram explaining one example of a method for producing a semiconductor device of the invention, and illustrates a state where a resist film is formed on the titanium film, and a hole pattern is formed in the titanium film.
Figure 6:
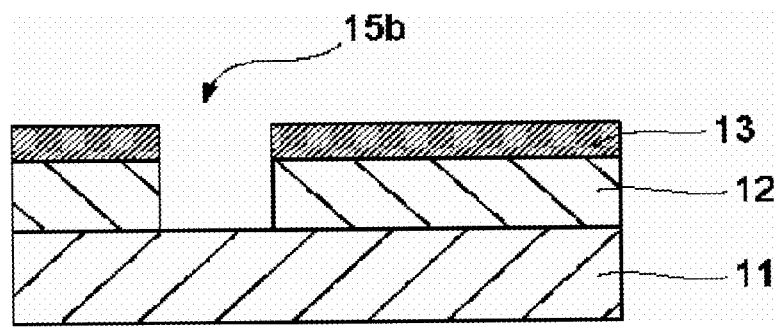
FIG. 6 is a schematic diagram explaining one example of a method for producing a semiconductor device of the invention, and illustrates a state where the hole pattern is also formed in the interlayer insulating film.

An interlayer insulating film 12 was formed on a silicon substrate 11 as illustrated in FIG. 3, and a titanium film 13 was formed on the interlayer insulating film 12 in accordance with a sputtering method as illustrated in FIG. 4. Sequentially, a resist pattern 14 was formed by an ArF liquid immersion exposure as illustrated in FIG. 5, and using the resist pattern 14 as a mask, the titanium film 13 was subjected to patterning by reactive ion etching so as to form an opening 15*a*. The reactive ion etching was continuously preformed so as to remove the resist pattern 14, as well as forming an opening 15*b* in the interlayer insulating film 12 using the titanium film 13 as a mask as illustrated in FIG. 6.

Figure 7:
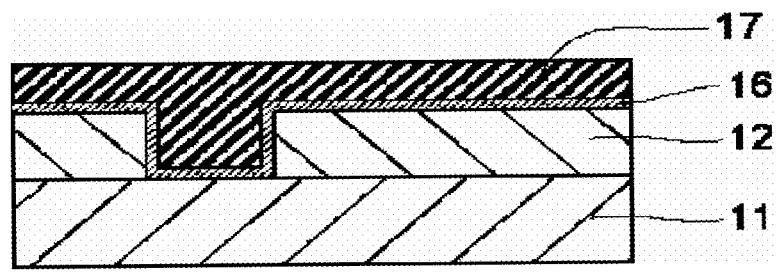
FIG. 7 is a schematic diagram explaining one example of a method for producing a semiconductor device of the invention, and illustrates a state where a Cu film is formed on the interlayer insulating film to which the hole pattern has been formed.
Figure 8:
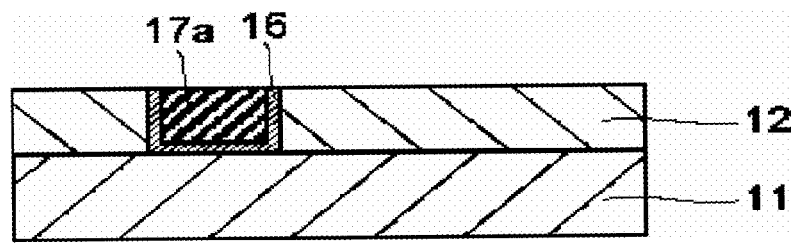
FIG. 8 is a schematic diagram explaining one example of a method for producing a semiconductor device of the invention, and illustrates a state where the Cu deposited on the interlayer insulating film other than on the hole pattern is removed.

Thereafter, the titanium film 13 was removed by a wet treatment, and a TiN film 16 was formed on the interlayer insulating film 12 in accordance with a sputtering method as illustrated in FIG. 7, and a Cu film 17 was sequentially formed on the TiN film 16 in accordance with an electroplating method. As illustrated in FIG. 8, the surface was smoothened by CMP while leaving only a barrier metal and the Cu film (first metal film) in a trench corresponding to the opening 15*b* (FIG. 6) so as to form a wiring 17*a* of a first layer.

Figure 9:
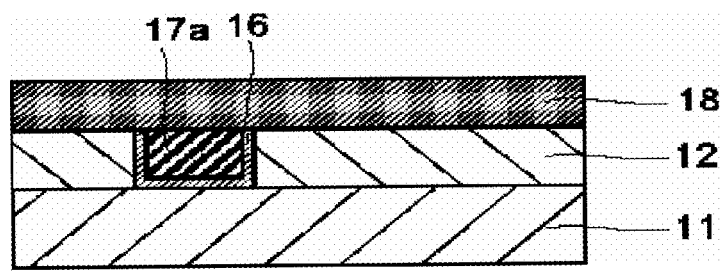
FIG. 9 is a schematic diagram explaining one example of a method for producing a semiconductor device of the invention, and illustrates a state where an interlayer insulating film is formed on the Cu plug formed in the hole pattern and on the TiN film.
Figure 10:
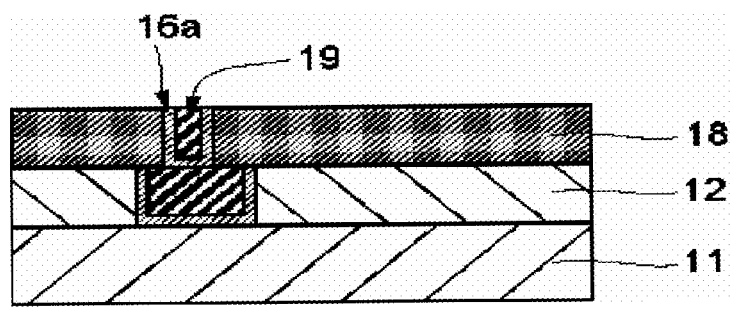
FIG. 10 is a schematic diagram explaining one example of a method for producing a semiconductor device of the invention, and illustrates a state where a hole pattern is formed in the interlayer insulating layer as the surface layer, and a Cu plug is formed therein.

Thereafter, an interlayer insulating film 18 was formed on the wiring 17*a* of the first layer as illustrated in FIG. 9, and then, as illustrated in FIG. 10, onto the wiring 17*a* of the first layer, a Cu plug (second metal film) 19 and a TiN film 16*a* which would be connected with a wiring of an upper layer formed later were formed in the same manner as illustrated in FIGS. 3 to 8.

Figure 11:
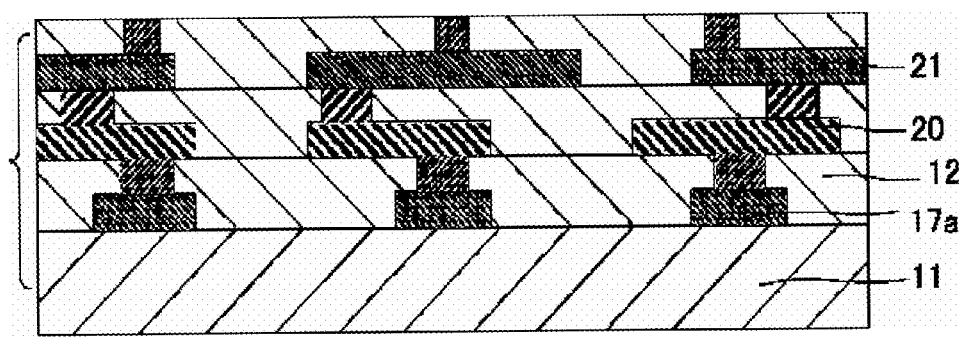
FIG. 11 is a schematic diagram explaining one example of a method for producing a semiconductor device of the invention, and illustrates a state where a three-layered wiring is formed.

By repeating each aforementioned process, a semiconductor device having a multi-layered wiring structure containing the first layer wiring 17*a*, the second layer wiring 20 and the third layer wiring 21 disposed on the silicon substrate 11 was formed as illustrated in FIG. 11. Note that, barrier metal layers each formed under each wiring were not illustrated in FIG. 11.

In Example 8, the resist pattern 14 was a resist pattern formed by using Resist Composition D of Example 6. Moreover, the interlayer insulating film 12 was formed with a low dielectric constant material having a dielectric constant of 2.7 or less, e.g. a porous silica film (CERAMATE NCS, manufactured by JGC Catalysts and Chemicals Ltd., dielectric constant: 2.25), or a fluorocarbon film (dielectric constant: 2.4) accumulated in accordance with a RFCVD method (power: 400 W) using a mixed gas of $C_4F_8$ and $C_2H_2$ or $C_4F_8$ gas as a source.

According to an aspect of the invention, there are provided: a monomer which enables to attain high sensitivity at a small usage amount of an acid generating agent and enables fine processing without surface or side face roughness; a resin containing the monomer unit; a resist composition containing the resin; and a method for manufacturing a semiconductor using the resin composition. There are also provided: a monomer which reduces risks for elution or out gassing, is effectively applied for ArF liquid immersion exposure as well as an EUV exposure method which is regarded as a next generation lithographic technique, and contributes to mass-production of devices; a resin containing the monomer unit; a resist composition containing the resin; and a method for manufacturing a semiconductor using the resist composition.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A monomer, which is represented by General Formula I:

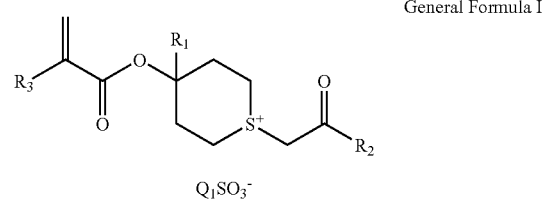

General Formula I wherein, each of $R_1$ and $R_3$ is either —H group or —CH$_3$ group, and $R_1$ and $R_3$ are identical or different to each other; $R_2$ is either a phenyl group or an adamanthyl group; and Q1 is a C1-4 perfluoroalkyl group.

2. A resin comprising:
a sulfonium salt-containing side chain,
wherein the resin comprises a monomer represented by General Formula 1 as a constitutional unit:

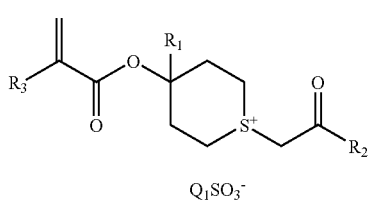

General Formula I wherein, each of $R_1$ and $R_3$ is either —H group or —CH$_3$ group, and $R_1$ and $R_3$ are identical or different to each other; $R_2$ is either a phenyl group or an adamanthyl group; and Q1 is a C1-4 perfluoroalkyl group.

3. A resist composition, comprising:
a resist base resin which comprises a resin comprising a sulfonium salt-containing side chain,
wherein the resin comprises a monomer represented by General Formula I as a constitutional unit:

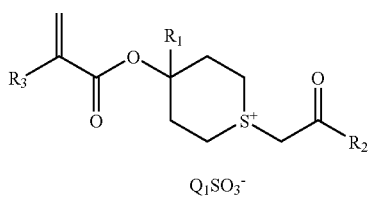

General Formula I wherein, each of $R_1$ and $R_3$ is either —H group or —CH$_3$ group, and $R_1$ and $R_3$ are identical or different to each other; $R_2$ is either a phenyl group or an adamanthyl group; and Q1 is a C1-4 perfluoroalkyl group.

4. The resist composition according to claim 3, wherein the resist base resin further comprises a monomer unit containing an alicyclic group reactive to an acid in a side chain of the resist base resin and a monomer unit containing a lactone group in a side chain of the resist base resin.

5. The resist composition according to claim 4, wherein the alicyclic group reactive to an acid is a 2-alkyl-2-adamanthyl group.

6. A method for manufacturing a semiconductor device, comprising:
forming a resist film on a surface to be processed;
selectively exposing the resist film with exposure light in the condition of an atmospheric air, a vacuumed air, or liquid immersion; and
developing the resist film so as to form a pattern of the resist film,
wherein the resist film is formed from a resist composition, the resist composition comprising a resin which comprises a sulfonium salt-containing side chain,
wherein the resin comprises a monomer represented by General Formula I as a constitutional unit:

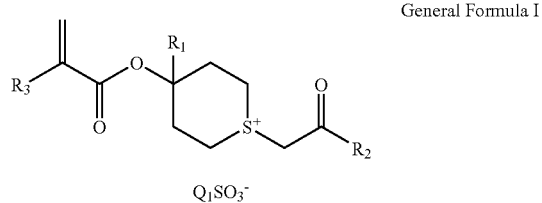

General Formula I wherein, each of $R_1$ and $R_3$ is either —H group or —CH$_3$ group, and $R_1$ and $R_3$ are identical or different to each other; $R_2$ is either a phenyl group or an adamanthyl group; and Q1 is a C1-4 perfluoroalkyl group.

7. The method for producing a semiconductor device according to claim 6, wherein the exposing is exposure of the exposure light in the condition of the liquid immersion, and a medium of the liquid immersion is either water or a liquid having higher refractive index with respect to the light having a wavelength of 193 nm than that of water.

* * * * *